United States Patent [19]

German et al.

[11] Patent Number: 5,830,730
[45] Date of Patent: Nov. 3, 1998

[54] ENHANCED ADENOVIRUS-ASSISTED TRANSFECTION COMPOSITION AND METHOD

[75] Inventors: Michael S. German; Francis C. Szoka, Jr., both of San Francisco, Calif.

[73] Assignee: The Regents of the University of California, Oakland, Calif.

[21] Appl. No.: 852,934

[22] Filed: May 8, 1997

[51] Int. Cl.$^6$ .......................... C12N 15/63; C12N 15/11; C12N 7/00
[52] U.S. Cl. .................................. 435/172.3; 435/235.1; 536/23.1
[58] Field of Search .............................. 435/172.3, 235.1; 536/23.1

[56] References Cited

U.S. PATENT DOCUMENTS 5,661,025  8/1997  Szoka, Jr. et al. ................... 435/172.3

FOREIGN PATENT DOCUMENTS

WO 9521259  8/1995  WIPO .

OTHER PUBLICATIONS

Al Fasbender et al., "Complexes of Adenovirus with Polycationic Polymers and Cationic Lipids Increase the Efficiency of Gene Transfer in Vitro and in Vivo", The Journal of Biological Chemistry, vol. 272, No. 10, Issue of Mar. 7, 1997, pp. 6479–6489.

*Primary Examiner*—George C. Elliott
*Assistant Examiner*—John S. Brusca
*Attorney, Agent, or Firm*—Nathan P. Koenig

[57] ABSTRACT

A composition for transfecting eukaryotic cells comprising a cationic polymer which has protonatable groups which serve to buffer the acidic endosome, protecting the endocytosed polynucleotide from degradation and a viral agent is used to target uptake into and/or lysis from endosomes in the desired eukaryotic cell. By co-infecting the eukaryotic cells with cationic polymer, polynucleotide, and the viral agent, the polynucleotide is brought into the cell and then released. Preferably, polyamidoamine dendrimers are used as the cationic polymer and adenovirus is used as the viral agent. The dendrimers help associate plasmid DNA with the adenovirus, which then provokes receptor-mediated endocytosis. Within the endosome, the tertiary amine groups of the dendrimer buffer the pH change in the endosome. Then, the endosomalytic activity of the adenovirus releases the plasmid DNA into the cell. Also preferably, the adenovirus and the dendrimers are mixed before addition to the polynucleotide and the cells are washed after about 1.5 hours of incubation.

18 Claims, 1 Drawing Sheet

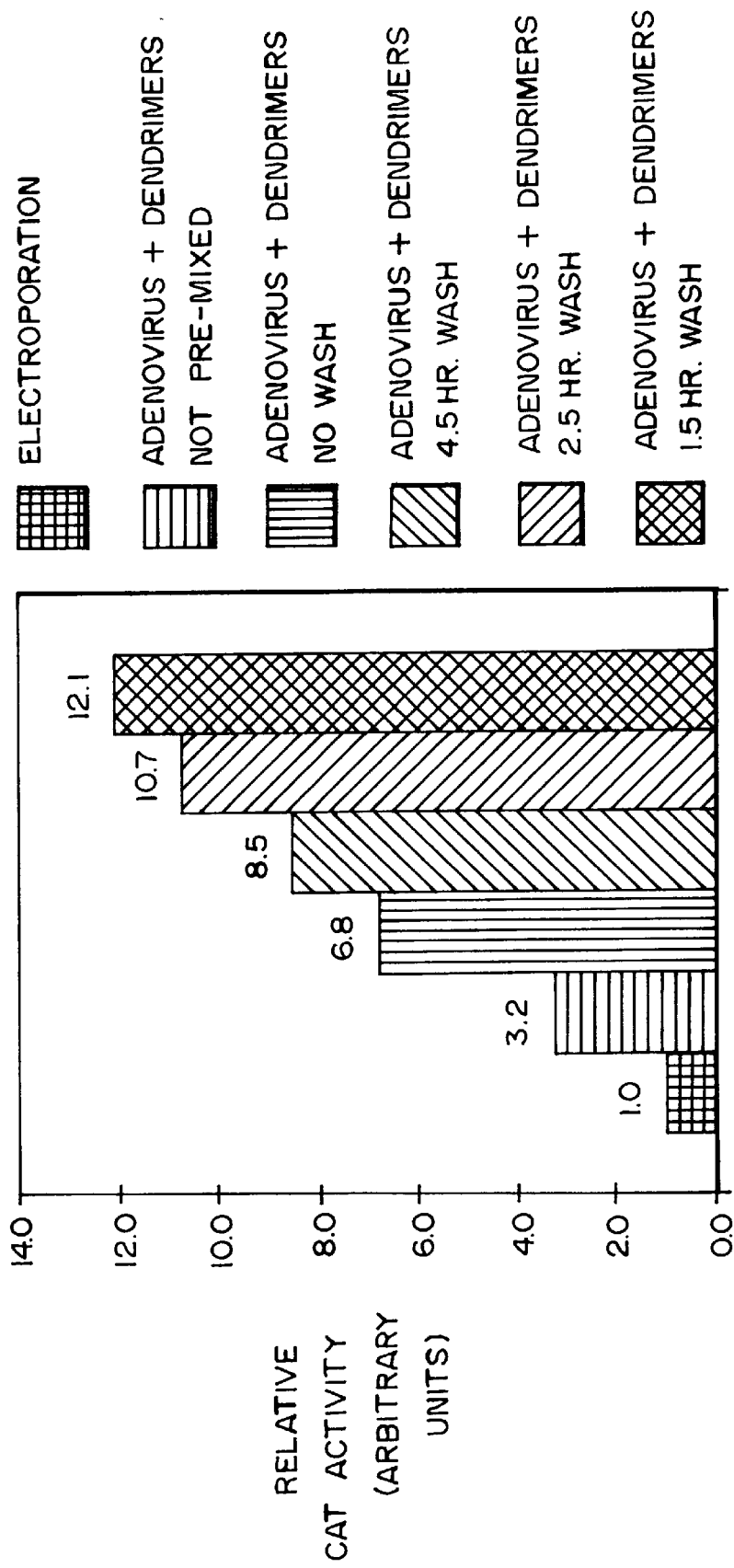

ENHANCED ADENOVIRUS-ASSISTED TRANSFECTION COMPOSITION AND METHOD

FIELD OF THE INVENTION

The invention generally relates to the field of gene therapy and in particular to the transfection of eukaryotic cells assisted by complexes of adenovirus and certain cationic polymers.

BACKGROUND OF THE INVENTION

Modern genetic engineering represents a powerful tool both for the fundamental study of molecular biology discussed above and for hopes of gene therapy to treat disease. However, the transfection of foreign genes into eukaryotic cells can still pose significant problems. Even though a range of techniques including calcium phosphate, electoporation, microinjection and osmotic shock have met with some success in vitro, none have proven suitable for in vivo applications. Further, certain types of cells have proven especially difficult to transfect. For example, pancreatic β-cells have transfection efficiencies of only between 10 and 20% with electroporation under the optimal prior art protocols. This technique yields even poorer results in adult β-cells and essentially does not work in intact islets. As such, molecular studies are restricted to dispersed fetal islets; the relatively low transfection efficiencies results in significant effort and cost for each study, and does not offer realistic opportunities for gene therapy.

Another method that represents promise is adenovirus-assisted transfection. These techniques offer the advantage of being useful with primary cells and cell lines that are both dividing or non-dividing. Under the direct approach, a recombinant adenovirus is produced and used to infect and transfer the exogenous genetic material to a host eukaryotic cell. This represents some risk, however, since a live virus is employed. A safer approach relies on the ability of adenovirus to provoke a receptor mediated endocytosis response wherein desired macromolecules are internalized.

Prior art enhancements to adenovirus-assisted transfection strategies have included the use of various cations to independently target the negatively-charged nucleic acids to the cells, or the cation-DNA compex is covalently linked to the virus. Early examples of such compositions include polymers such as polybreen and DAE-xtran while later approaches have dealt with cationic lipids and cationic polymers such as polylysine. The moderate successes experienced using adenovirus-cation complexes imply that they do hold potential. However, these adenovirus-assisted examples are far from satisfactory. For example, in β-cells, the transfection efficiencies obtained with prior art adenovirus methods remains less than that obtained with electoporation.

Accordingly, there remains a need for a system of transfection having increased efficiencies. There also remains a need for a transfection strategy which improves the transfer of genetic information from the endosome. This invention satisfies these and other needs.

SUMMARY OF THE INVENTION

This invention is a composition for delivering a polynucleotide to a eukaryotic cell comprising a complex of a viral agent, a cationic polymer having groups protonatable at a pH of less than 7.0, and the polynucleotide. The invention also comprises methods of using this composition. Preferably, the complex comprises adenovirus, polyamidoamine dendrimer polycation and the polynucleotide. More preferably, the dendrimer and polynucleotide are complexed in a ratio of about 1:4.

BRIEF DESCRIPTION OF THE DRAWINGS

FIG. 1 illustrates relative levels of transfective activity for various embodiments of the invention as compared to the best prior art technique. CAT activity was measured on 10 mcg protein. The activity of the islets transfected by electroporation was arbitrarily set as 1, and the activity of the other islets was determined relative to this value.

DETAILED DESCRIPTION OF THE INVENTION

This invention comprises a combination of two techniques. First, a cationic polymer is used to ionically condense a polynucleotide, enhancing uptake into the cell via endosomes. In addition, these cationic polymers have protonatable groups which serve to buffer the acidic endosome, protecting the endocytosed polynucleotide from degradation. Second, a viral agent is used to target uptake into and lysis from endosomes in the desired eukaryotic cell. By co-infecting the eukaryotic cells with cationic polymer, polynucleotide, and the viral agent, the polynucleotide is brought into the cell and then released.

In a preferred embodiment, polyamidoamine dendrimers are used as the cationic polymer and adenovirus is used as the viral agent. The dendrimers help associate plasmid DNA with the adenovirus, which then provokes receptor-mediated endocytosis. Within the endosome, the tertiary amine groups of the dendrimer buffer the pH change in the endosome. Then, the endosomalytic activity of the adenovirus releases the plasmid DNA into the cell. It may also be desirable to lyophilize the cationic polymer/viral agent/polynucleotide complex before contacting the eukaryotic cell. Lyophilization can increase the stability of the complex for storage and can enhance the delivery characteristics.

The viral agents of the invention comprises viruses or virus analogs that have the characteristic of targeting uptake into and/or lysis from endosomes in the target cell. Some examples are adenovirus, adeno-associated virus, herpes simplex virus, sendai virus, semliki virus, influenza virus, and retroviruses. In each of these examples, it is preferable to use an inactivated form of the virus in which the viral genome has been disrupted but the abilty to trigger uptake retained. Accordingly, suitable virus analogs may include simply the viral protein coat or capsid, or even specific protein sequences found to provoke uptake or lysis. Suitable adenovirus species share the characteristics of provoking receptor-mediated endocytosis and having endolytic activity. The adenovirus may be replication-competent or deficient. Suitable species of adenovirus include human strains, such as Ad5, Ad-CFTR, and Ad-dl312, and the chicken adenovirus CELLO. It may also be desirable to modify the adenovirus to improve endocytosis or lysis. It is generally preferable to employ adenovirus that is replication-deficient to avoid interference with host cell functionality. The adenovirus may be rendered replication-deficient by any suitable technique, including chemical modification, genetic modification or UV irradiation. Alternatively, the adenovirus genome can be removed entirely leaving only the protein capsid. Indeed, with this invention the viral genome has been destroyed with psoralin and UV irradiation without significant loss of transfection efficiency. Likewise, synthetic, modified or naturally occurring protein analogs of the adenovirus capsid may be used instead.

In general, the invention is directed to the transfer of plasmid DNA but virtually any species of nucleic acid may be used, including DNA, RNA or PNA. Moreover, the nucleic acid may be of any reasonable length and can be single stranded, double stranded, triple stranded or mixtures thereof. The nucleic acids may also be modified or substituted using synthetic analogs.

An important characteristic of the cationic polymers of this invention is existence of groups which can be protonated in the endosome to enhance the escape of the polynucleotide. Preferably, these polymers have at least two types of positively charged groups: The first is predominately positively charged at pH 7.4 and the second becomes predominantly positively charged below pH 7.4 and preferably below 6.5. The first type of positively charged groups mediates binding of the polymer to the virus and promotes binding of the virus to the cell surface. Since the second type becomes positively charged in the endosome, it buffers the pH change in the endosome. Likely, this slows down the rate of movement of the virus through the endosomal compartment into the lysosome where it is degraded. The slower movement increases the probability that the virus can escape from the endosome. Further, as the pH is buffered in the endosome, the second type becomes protonated and thus positively charged. The new positive charges on the polymer may cause polymer expansion and contribute to escape of the virus, and consequently the polynucleotide, from the endosome. Even if a different mechanism is at work, an important feature is the existence of groups on the cationic polymer which can become protonated in the endosome.

Accordingly, suitable cationic polymers have groups comprising primary amines and secondary or tertiary amines. A preferred example of such cationic polymers are dendrimers such as those disclosed in U.S. Pat. Nos. 4,507,466, 4,558,120, 4,568,737, 4,587,329, 4,631,337, 4,694,064, 4,713,975, 4,737,550, 4,871,779, and 4,857,599 to Tomalia, D. A., et al. which are hereby incorporated by reference. Dendrimers have tertiary amines which have a pKa of 5.7. Improved results can be obtained by using fractured dendrimers which have been chemically or heat treated to remove some of the tertiary amines. Other suitable cations include polyethyleneimine (PEI) which has tertiary amines with a pKa of 5.9 and poly(4'-aza-4'-methylheptamethylene D-glucaramide) which has tertiary amines with a pKa of 6.0. Tests with PEI result in a two-fold improvement over dendrimers without any increase in cell toxicity. Suitable polymers may also have a molecular weight as low as 3000 MW.

Yet other suitable cations may include those that contain a mixture of quaternary amines and secondary or tertiary amines. For example, a polypeptide consisting of lysines, ornithines or arginines (which are protonated at pH 7.4) and histidine or aminopyridine or aminotyrosine (which become protonated below pH 7.4 and preferably below pH 6.5). The preferred ratio of first type to second type charged groups may range between 4:1 to 1:4.

In other embodiments where the polymers can be associated with the virus without electrostatic interactions, the cationic polymer should not require groups of the first type. In these instances, the polymer should only require groups that become protonated at a pH below 7.0, preferably below 6.5.

Employing, a catonic polymer for its ability to buffer the endosome represents a significant departure from the teaching of the prior art. For example, previous attempts to enhance adenovirus-assisted transfection have used polycations such as polylysine. However, polylysine has terminal amines that have a pKa of 10.5, and thus, do not significantly enhance transfection.

In general, this invention may be used to transfect any type of eukaryotic cell. The invention is particularly useful with cell types which are difficult to transfect using prior art methods, such as β-cells. Other suitable cells include hepatocytes, muscle cells, endothelial cells, fibroblasts and neuronal cells.

Results

To test transfection efficiencies, fetal rat islet cells were transfected with a DNA plasmid (−410 Insulin-CAT) with the bacterial gene chloramphenicol-acetyl transferase (CAT) driven by the rat insulin I promoter. CAT enzyme activity was then used as a guage of transfection activity. The 21 day fetal rat pancreases were harvested in Hanks Balanced Salt Solution, minced and digested with collagenase. The digest was resuspended in RPMI with 10% FBS and pen/strep (RPM) and incubated at 37 degrees for 4 hours. The islets were then trypsinized for ten minutes, replated in RPMI and incubated for an additional 3 hours. Cells were then transfected with a combination of −410 Insulin-CAT DNA, dendrimer and virus. Replication deficient Adenovirus 5 dI 342 was grown in the complimentary cell line HEK 293. Infected cells were harvested and the virus particles released by three freeze/thaw cycles. The virus was then purified on a cesium chloride gradient and subsequently dialyzed against RPMI to remove any residual cesium. Final viral concentrations were determined by performing a BIO-RAD protein assay and using the conversion factor of 1 mg/ml protein=$3.4 \times 10^{12}$ virus particles/ml. The dendrimers used were as described above.

The Dendrimer:DNA solutions were made by diluting 24 mcg of dendrimers in 170 mcl OPTI-MEM-1 media (serum free). 6 mcg of plasmid DNA was diluted in 330 mcl OPTI-MEM-1. These two solutions were mixed and incubated at room temperature for 30 mins. Preferably, the ratio of DNA to dendrimer is between about 1:4 and 4:1 and more preferably, is about 4:1. Adenovirus 5 dI 342 was diluted in mcl OPTI-MEM-1 to yield a final concentration of approximately $1-10 \times 10^{11}$ virus particles/ml. The islets were suspended in OPTI-MEM-1 media, approximately 2–3 pancreases in 1 ml media per transfection. (For adult islet transfections, approximately 200 adult mouse islets were suspended in 1 ml OPTI-MEM-1 media per transfection). The islets were placed in one well of a six-well plate and 500 mcl of the dendrimer/DNA solution was added. Finally, 100 mcl of diluted adenovirus were added (alternatively, the adenovirus was added directly to the dendrimer:DNA solution). The islets were incubated overnight and the following day 3 ml RPMI is added (alternatively, the islets were washed with RPMI three times after 1.5, 2.5, or 4.5 hrs, resuspended in 4 ml RPMI and plated in six-well plates). Transfected islets were incubated for approximately 36 hours following transfection and a CAT enzyme assay was performed on 10 mcg protein for 2 hours. CAT expression levels were compared for transfections using electroporation, liposomes, polycationic starburst dendrimers or naked DNA.

As shown in FIG. 1, the combination of dendrimers with adenovirus gave the highest expression levels: 3.2 fold higher than the optimal prior art protocol, electroporation, and even greater enhancement over dendrimers alone, adenovirus alone, liposomes, calcium phosphate, adenovirus plus liposomes, adenovirus plus electroporation and naked DNA.

Notably, transfection using naked DNA, lipofectin, dendrimers alone, or adenovirus alone yield CAT activity significantly lower than electroporation. Further, mixing the adenovirus with the DNA/dendrimer solution before addition to the islet cells improves CAT signal approximately two-fold over not pre-mixing, and approximately seven fold over electroporation.

High level transfection is dependent upon intact viral particles but not the viral genome, since adenovirus was still effective at enhancing transfection following chemical disruption of the adenoviral DNA. By co-staining for insulin and the transfected transgene, it was found that the dendrimer/adenovirus method transfects at least 85% of the cultured β-cells. Under optimal conditions, over 90% efficiency can be achieved.

Although transfection efficiency generally increases with incubation time, microscopic examination of the transfected cells revealed significant injury and "rounding up" after long incubation times. As shown in FIG. 1, control of incubation time by washing off the dendrimer/DNA/adenovirus complex can decrease toxicity. The optimal time of incubation with the dendrimer/DNA/adenovirus complex appears to be 1.5 hours, which resulted in nearly a doubling of CAT activity over leaving the virus/dendrimer solution on the islet cells, and a full 12 fold improvement over the previous optimal transfection technique of electroporation.

In other experiments, the dendrimer/DNA/adenovirus complex was used to transfect intact adult mouse islets. Mice were anesthetized and the pancreas inflated with collagenase. The insufflated pancreas was removed and allowed to digest. The islets were initially purified on a dextran gradient and the resulting islets were further purified by hand picking. Islets were then suspended in RPMI and incubated at 37 degrees for 4–16 hours. A plasmid (CMV-CAT), having the cytomegalovirus (CMV) promoter driving the cDNA for the bacterial enzyme chloramphenicol-acyl transferase, was also used. Use of the dendrimer/DNA/adenovirus successfully transfected the adult mouse islets with efficiency equivalent to the fetal islets for both CMV-CAT and –410 Insulin-CAT. In yet other experiments, the use of the dendrimer/DNA/adenovirus complex generated an even greater enhancement over prior art transfective techniques in the β cell tumor line, βTC3 and primary cultured α cells were also successfully transfected.

To test the percent of cells transfected, the 21 day fetal rat islet cells were transfected with a plasmid (–410 bp Insulin-Tag) encoding the Simian Virus 40 (SV40) large T antigen (Tag) driven by the rat insulin I promoter. Since T-antigen is intranuclear, co-staining for insulin and T-antigen allows determination of transfection efficiency. The cells were transfected with the –410 Insulin-Tag DNA as described above. Transfected islets were plated in culture-chamber slides coated with Matrigel immediately after transfection. After 36 hours of incubation the slides are fixed, and stained by immunofluorescence. Tag immunoreactivity was found only in insulin positive cells. Of insulin positive cells, 85% were Tag positive. This compares very favorably with cells transfected by the older electroporation technique which gave 11% transfection efficiency. There is also a significant decrease in toxicity for the β-cells: there were less than half as many total insulin positive cells in the electroporated cultures.

Although the invention has been described primarily with regard to ex vivo techniques, it may be tailored for in vivo use, either by transplanting cells transfected ex vivo, or by transfecting intact cells in vivo. Transfection in vivo would involve the same mix of virus/cationic polymer/polynucleotide applied directly to the cells.

Thus, this invention represents several advantages: 1) high efficiency of transfection; 2) ability to transfect many cells types including primary cultured cells, cell lines and intact islets; 3) a new viral agent does not need to be constructed for each experiment, simply a new bacterial plasmid can be constructed instead; 4) the viral DNA is not needed, and can be destroyed prior to infection, removing the potentially confounding variable of viral DNA sequences. This protocol can be used both to investigate the function of normal and diabetogenic β-cells, and also to alter β-cells genetically for therapeutic purposes. This protocol can also be used with any other suitable eukaryotic cell, both primary cells and cell lines.

What is claimed is:

1. A method for introducing a polynucleotide into a eukaryotic cell comprising contacting the cell with a complex comprising the polynucleotide, a viral agent and a polymer which has a net positive charge at pH 7.4 and which comprises protonatable groups that have a pKa of 7.4 or less.

2. The method of claim 1, wherein the step of contacting the cell with the complex comprises contacting the cell with a complex in which the viral agent consists of an adenovirus and in which the polymer consists of a dendrimer.

3. The method of claim 2, further comprising the step of washing the complex off the cell.

4. The method of claim 3, wherein the step of washing the complex off the cell comprises washing about 1.5 hours after contacting.

5. The method of claim 2, further comprising the step of first mixing the dendrimer and the adenovirus and then adding the polynucleotide to form the complex.

6. A composition for introducing a polynucleotide into a eukaryotic cell comprising a complex of the polynucleotide, a viral agent, and a polymer which has a net positive charge at pH 7.4 and which comprises protonatable groups that have a pKa of 7.4 or less.

7. The composition of claim 6, wherein the viral agent consists of an adenovirus.

8. The composition of claim 7, wherein the adenovirus consists of a replication-deficient adenovirus.

9. The composition of claim 6, wherein the polymer consists of a dendrimer.

10. The composition of claim 9, wherein the dendrimer has a plurality of amine groups and has been fractured to remove a portion of the amine groups.

11. The composition of claim 6, wherein the polymer consists of a polymer comprising a first type of charged groups and a second type of charged groups, wherein the first type is protonated at a pH of about 7.4 and the second type can become protonated at a pH below about 7.0.

12. The composition of claim 11, wherein the ratio of the number of first type groups to second type groups is between about 1:4 and 4:1.

13. The composition of claim 6, wherein the viral agent consists of an adenovirus and the polymer consists of a dendrimer.

14. The composition of claim 13, wherein the ratio of the number of dendrimers to polynucleotides is about 1:4.

15. The composition of claim 6, wherein the polymer consists of polyethyleneimine.

16. The composition of claim 6, wherein the polymer comprises the group consisting of poly(4'-aza-4'-methylheptamethylene D-glucaramide) and its analogs.

17. The composition of claim 6, wherein the complex is lyophilized.

18. The method of claim 1, wherein the complex is lyophilized.

* * * * *

UNITED STATES PATENT AND TRADEMARK OFFICE
CERTIFICATE OF CORRECTION

PATENT NO. : 5,830,730

DATED : November 3, 1998

INVENTOR(S) : German et al.

It is certified that error appears in the above-identified patent and that said Letters Patent is hereby corrected as shown below:

In column 1, line 11, please insert:

--This invention was made with Government support under Grant No. DK46052, awarded by the National Institutes of Health. The Government has certain rights in this invention.--

Signed and Sealed this

Fourth Day of May, 1999

Attest:

Attesting Officer

Q. TODD DICKINSON

Acting Commissioner of Patents and Trademarks